United States Patent [19]

Singer et al.

[11] Patent Number: 5,523,204
[45] Date of Patent: Jun. 4, 1996

[54] DETECTION OF NUCLEIC ACIDS IN CELLS BY STRAND DISPLACEMENT AMPLIFICATION

[75] Inventors: Robert H. Singer, Shrewsbury, Mass.; Jean Marie Mathys, New South Wales, Australia; Kenton L. Lohman, San Jose, Calif.

[73] Assignees: Becton Dickinson and Company, Franklin Lakes, N.J.; University of Massachusetts, Worcester, Mass.

[21] Appl. No.: 165,719

[22] Filed: Dec. 10, 1993

[51] Int. Cl.$^6$ .............................. C12P 10/34; C12Q 1/68
[52] U.S. Cl. ................................. 435/5; 935/77; 935/78
[58] Field of Search ................................ 435/5, 6, 91.2; 935/77, 78

[56] References Cited

U.S. PATENT DOCUMENTS

| | | | |
|---|---|---|---|
| 4,683,202 | 7/1987 | Mullis | 435/6 |
| 4,888,278 | 12/1989 | Singer et al. | 435/6 |
| 5,168,038 | 12/1992 | Tecott et al. | 435/6 |
| 5,270,184 | 12/1993 | Walker et al. | 435/91.2 |

FOREIGN PATENT DOCUMENTS

0524808A2  1/1993  European Pat. Off. .

OTHER PUBLICATIONS

Bagasra, O., et al., "Detection of Human Immunodeficiency Virus Type 1 Provirus in Mononuclear Cells by In Situ Polymerase Chain Reaction", 1992, *N.E.J. Med.*, vol. 326, No. 21, pp. 1385–1391.
Embleton, M. J., et al., "In–cell PCR from mRNA: Amplifying and Linking the Rearranged Immunoglobulin Heavy and Light Chain V–genes Within Single Cells", 1992, *Nucleic Acids Res.*, vol. 20, No. 15, pp. 3831–3837.
Embretson, J., et al., "Analysis of Human Immunodeficiency Virus–Infected Tissues by Amplification and in Situ Hybridization Reveals Latent and Permissive Infections at Single–cell Resolution", 1993, *Proc. Natl. Acad. Sci. USA*, vol. 90, pp. 357–361.
Haase, A. T., et al., "Amplification and Detection of Lentiviral DNA Inside Cells", 1990, *Proc. Natl. Acad. Sci. USA*, vol. 87, pp. 4971–4975.
Lawrence, J. B., et al., "Subcellular Localization of Low–abundance Human Immunodeficiency Virus Nucleic Acid Sequences Visualized by Fluorescence In Situ Hybridization", 1990, *Proc. Natl. Acad. Sci. USA*, vol. 87, pp. 5420–5424.
Lawrence, J. B., et al., "Highly Localized Tracks of Specific Transcripts Within Interphase Nuclei Visualized by In Situ Hybridization", 1989, *Cell*, vol. 57, pp. 493–502.
Nuovo, G. J. et al., "Rapid In Situ Detection of PCR–Amplified HIV–1 DNA", 1992, *Diagnostic Molec. Pathol.*, vol. 1, No. 2, pp. 98–102.
Nuovo, G. J., et al., "Detection of Human Papillomavirus DNA in Formalin–fixed tissues by In Situ Hybridization After Amplification by Polymerase Chain Reaction", 1991, *Am. J. Pathol.*, vol. 139, No. 4, pp. 847–854.
Nuovo, G. J. et al., "Rapid Communication: An Improved Technique for the In Situ Detection of DNA after Polymerase Chain Reaction Amplification", 1991, *Am. J. Pathol.*, vol. 139, No. 6, pp. 1239–1244.
Patterson, B. K., et al., "Detection of HIV–1 DNA and Messenger RNA in Individual Cells by PCR–Driven In Situ Hybridization and Flow Cytometry", 1993, *Science*, vol. 260, pp. 976–979.
Saiki, R. K., et al., "Enzymatic Amplification of β–Globin Genomic Sequences and Restriction Site Analysis for Diagnosis of Sickle Cell Anemia", 1985, *Science*, vol. 230, pp. 1350–1354.
Walker, G. T., et al., "Isothermal In Vitro Amplification of DNA by a Restriction Enzyme/DNA Polymerase System", 1992, *Proc. Natl. Acad. Sci. USA*, vol. 89, pp. 392–396.
Walker, G. T. et al., "Strand Displacement Amplification—An Isothermal, In Vitro DNA Amplification Technique", 1992, *Oxford Univ. Press*, vol. 20, No. 7, pp. 1691–1696.
Bagasra, et al., "Human Immunodeficiency Virus Type 1 Provirus Is Demonstrated in Peripheral Blood Monocytes In Vivo: A Study Utilizing and In Situ Polymerase Cahin Reaction", 1993, *AIDS Research and Human Retroviruses*, 9:69–75.
Lohman, et al., "Detection of Intracellular HIV–1 Proviral DNA Sequences by Strand Displacement Amplification and In Situ Hybridization", 1993, *Molecular Biol. of the Cell*, vol. 4 Suppl., No. 656.
Walker, "Empirical Aspects of Strand Displacement Amplification", 1993, *PCR Methods and Applications*, 3:1–6.
European Search Report, EP 94 30 9308; 31 Mar. 1995.

*Primary Examiner*—Stephanie W. Zitomer
*Attorney, Agent, or Firm*—Fish & Richardson

[57] ABSTRACT

Strand Displacement Amplification for amplification of nucleic acid target sequences in situ in cells in suspension, on slides or in tissues. Excellent specimen morphology is preserved, and either DNA targets, or RNA targets, or both may be selectively amplified. In situ amplification by SDA is compatible with immunochemical techniques, so that both amplification of target sequences and immunological staining can be performed on the same specimen.

44 Claims, 4 Drawing Sheets

SDA

PCR

DETECTION OF NUCLEIC ACIDS IN CELLS BY STRAND DISPLACEMENT AMPLIFICATION

FIELD OF THE INVENTION

The present invention relates to amplification of nucleic acids and in particular to amplification of nucleic acids in morphologically intact cells.

BACKGROUND OF THE INVENTION

Nucleic acid amplification techniques have provided powerful tools for detection and analysis of small amounts of nucleic acids. The extreme sensitivity of such methods has lead to attempts to develop them for early diagnosis of infectious and genetic diseases, isolation of genes for analysis, and detection of specific nucleic acids in forensic medicine. Nucleic acid amplification techniques can be grouped according to the temperature requirements of the procedure. The polymerase chain reaction (PCR), ligase chain reaction (LCR) and transcription-based amplification require repeated cycling of the reaction between high (85° C.–100° C.) and low (30° C.–40° C.) temperatures to regenerate single stranded target molecules for amplification. In contrast, methods such as Strand Displacement Amplification (SDA), self-sustained sequence replication (3SR) and the Qβ replicase system are isothermal reactions which can be performed at a constant low temperature (usually about 30°–40° C.).

One of the best-known nucleic acid amplification methods is the Polymerase Chain Reaction (PCR). This method is described by R. K. Saiki, et al. (1985. *Science* 230, 1350–1354) and in U.S. Pat. No. 4,683,195, U.S. Pat. No. 4,683,202 and U.S. Pat. No. 4,800,159. Briefly, to amplify a target sequence using the PCR, two primers complementary to sequences flanking the target sequence are hybridized (one to each of the opposite complementary strands) and extended, using the target sequence as a template, by addition of deoxyribonucleotides and a DNA polymerase. After extension, the temperature of the reaction is raised to separate the newly-synthesized strand from the template, then lowered to reanneal the primers and repeat the extension process. Due to the characteristic cycling of the reaction temperature, the PCR requires the use of a heat stable polymerase such as Taq polymerase.

In contrast, Strand Displacement Amplification (SDA) is an isothermal method of nucleic acid amplification in which extension of primers, displacement of single stranded extension products, annealing of primers to the extension products (or the original target sequence) and subsequent extension of the primers occurs concurrently in the reaction mix. This is in contrast to the PCR, in which the steps of the reaction occur in discrete phases or cycles as a result of the temperature constraints of the reaction. SDA is based upon 1) the ability of a restriction endonuclease to nick the unmodified strand of a hemiphosphorothioate form of its double stranded recognition site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature (usually about 37° C.). Production of each new copy of the target sequence consists of five steps: 1) binding of amplification primers to an original target sequence or a displaced single-stranded extension product previously polymerized, 2) extension of the primers by exonuclease deficient (exo⁻) klenow polymerase incorporating an α-thio deoxynucleoside triphosphate, 3) nicking of a hemiphosphorothioate double stranded restriction site, 4) dissociation of the restriction enzyme from the nick site, and 5) extension from the 3' end of the nick by exo⁻ klenow with displacement of the downstream non-template strand. Nicking, polymerization and displacement occur concurrently and continuously at a constant temperature because extension from the nick regenerates another nickable restriction site. When primers which hybridize to both strands of a double stranded target sequence are used, amplification is exponential, as the sense and antisense strands serve as templates for the opposite primer in subsequent rounds of amplification. SDA is described by G. T. Walker, et al. (1992a. *Proc. Natl. Acad. Sci. USA* 89, 392–396 and 1992b. *Nuc. Acids. Res.* 20, 1691–1696). Examples of restriction enzymes which nick their double stranded recognition sites when an α-thio dNTP is incorporated are HincII, HindII, AvaI, NciI and Fnu4HI. All of these restriction enzymes and others which display the required nicking activity are suitable for use in SDA. The Walker, et at. disclosures are hereby incorporated by reference and details of the SDA method are found in the following Examples.

Targets for amplification by SDA may be prepared by fragmenting larger nucleic acids by restriction with the endonuclease used in the SDA reaction (e.g., HincII). However, for in situ amplification it is most preferred that target nucleic acids having the selected restriction endonuclease recognition sites for nicking in the SDA reaction be generated as described by Walker, et al. (1992b, supra). This target generation scheme is also described in U.S. Pat. No. 5,270,184, the disclosure of which is hereby incorporated by reference. This method for generation of SDA-amplifiable target sequences comprises heat denaturing double stranded nucleic acids containing the target sequence and hybridizing four primers to the target sequence. Two of the primers ($S_1$ and $S_2$) are SDA amplification primers as defined below, with target binding sequences near their 3' ends and restriction enzyme recognition sites 5' to the target binding sequences. When both amplification primers are used amplification is exponential, however, use of only one amplification primer results in linear amplification of the target sequence. The other two primers ($B_1$ and $B_2$) are external primers as defined below and consist only of target binding sequences. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. Exonuclease deficient klenow polymerase (exo⁻ klenow polymerase) is then used to simultaneously extend all four primers in the presence of three deoxynucleoside triphosphates and one modified deoxynucleoside triphosphate (e.g., deoxyadenosine 5'-[α-thio]triphosphate dATP [αS]). Extension of $S_1$ and $S_2$ produces two extension products, $S_1$-ext and $S_2$-ext. Extension of $B_1$ and $B_2$ results in displacement of the downstream $S_1$ and $S_2$ extension products from the original target sequence template. The displaced, single stranded $S_1$ extension product serves as a target for binding of $S_2$ and $B_2$. Similarly, the displaced, single stranded $S_2$ extension product serves as a target for binding of $S_1$ and $B_1$. All four primers are then extended on the $S_1$-ext and $S_2$-ext templates to produce a second pair of extension products which are displaced by extension of the external primers as before. Binding and extension of complementary amplification primers on these displaced extension products results in synthesis of a complementary strand. This produces two double stranded nucleic acid fragments with hemimodified restriction enzyme recognition sites at each end which are suitable for amplification by SDA. The extended external primers hybridized to $S_1$-ext and $S_2$-ext form two larger double stranded fragments with hemimodified restriction enzyme recognition sites at only one end. As in SDA, the individual steps of the target generation reaction occur concurrently and continuously, generating target sequences with the required recognition sequences at the ends for nicking by the restriction enzyme in SDA. As all of the components of the SDA reaction are already present in the target generation reaction, target sequences generated automatically and continuously enter the SDA cycle and are amplified.

In situ methods of nucleic acid analysis allow detection and localization of specific nucleic acid sequences within morphologically intact cells. In situ methods of nucleic acid analysis have conventionally been accomplished by direct hybridization of labeled probes, for example as described in U.S. Pat. No. 4,888,278. However, such direct hybridization methods, while specific for the nucleic acid of interest, may not be sufficiently sensitive to detect very low copy numbers of the nucleic acid in all cases. As a means for detecting very low copy numbers, in situ amplification of the target sequence prior to in situ detection has been of great interest. In situ nucleic acid amplification methods have the potential to be more sensitive that conventional solution amplification because the cell may concentrate the amplification product, thereby allowing detection of fewer molecules than is possible when amplification products are free to diffuse or are diluted by the contents of cells which do not contain the sequence of interest. Because the nucleic acid is not extracted from the cell prior to the analysis, in situ methods provide information as to which cells in a population contain a particular nucleic acid and further permit analysis of the nucleic acid in the context of the biochemical and morphological characteristics of the cell. Prior to the present invention, in situ amplification methods have only been developed for the PCR (O. Bagasra and R. Pomerantz. 1993. *AIDS Research and Human Retroviruses* 9(1), 69–76; G. Nuovo, et al. 1992. *Diag. Molec. Pathol.* 1(2), 98–102; M. J. Embleton, et al. 1992. *Nuc. Acids Res.* 20(15), 3831–3837; J. Embretson, et al. 1993. *Proc. Natl. Acad. Sci. USA* 90, 357–361; P. Komminoth, et al. 1992. *Diag. Molec. Pathol.* 1(2), 85–97; K. P. Chile, et al. 1992. *J. Histochem. Cytochem.* 40(3), 333–341; Haase, et al. 1990. *Proc. Natl. Acad. Sci. USA* 87, 971–4975; O. Bagasra, et al. 1992. *New Engl. J. Med.* 326(21), 1385–1391; Patterson, et al. 1993. *Science* 260, 976–979). However, the multiple cycles of heating and stringent hybridization conditions required by the PCR to achieve its sensitivity are not well tolerated by tissues and cells. Diffusion of the amplified sequences out of the cells is increased by the repeated heating, resulting in increased diffuse signal throughout the sample. To attempt to reduce the loss of PCR products from the cell, long fixation times (15 hours to days) with cross-linking fixatives are considered essential for successful in situ amplification by the PCR. As a result of the extensive fixation, it is also considered critical to treat the fixed cells with protease prior to amplification (G. Nuovo, et al. 1992. *Diag. Molec. Pathol.* 1(2), 98–102).

The ability of SDA to amplify low copy-number target sequences at 37° C. made it desirable to attempt to develop methods for in situ nucleic acid amplification using this technique. However, the many significant differences between PCR and SDA amplification reaction protocols made it highly uncertain whether or not in situ amplification could be successfully performed at a constant, relatively low temperature to minimize destructive effects on the cellular morphology. Both the in situ PCR and in situ SDA employ fixing of the cells to maintain cell integrity. At the lower temperatures of SDA, nucleic acids within the fixed cell are therefore more stably crosslinked with proteins which may physically interfere with hybridization and prevent access of polymerase, probes and/or restriction enzymes to the target sequence. Access of polymerase and/or restriction enzymes to the probes or amplicons may also be inhibited by associated proteins, thus preventing amplification. In the PCR, it is likely that heating assists in partially or wholly reversing the fixation or the effects of fixation, releasing the associated proteins from the nucleic acids or decreasing their affinity and freeing them for amplification. No such release of interfering proteins would be expected in isothermal amplification reactions. In addition, the heating steps for the PCR may repetitively denature inter- and intra-strand hybridization allowing the primers better access to the target. No such repetitive heating occurs with SDA. Further, the phosphorothioates used in SDA may form disulfide bonds with cellular proteins, preventing access of reagents to the target.

Further, the amplification products of the PCR are generally larger in size than those produced by SDA. SDA amplification products would therefore be even more likely than PCR amplification products to diffuse out of the cell. It was not previously known whether or not the amplification products of SDA would be large enough to be retained by the cell after in situ amplification. Although in situ PCR amplification has been performed on formaldehyde-fixed cells, it was uncertain what affect fixing and the formaldehyde fixative itself would have on the particular enzymatic reactions required by SDA—e.g., nicking of a hemiphosphorothioate recognition site by a restriction enzyme and the displacing activity of exo⁻ klenow polymerase. Not only does the crosslinking which occurs in the fixing process potentially and unpredictably exclude certain molecules from the interior of the cell, formaldehyde is known to interact with nucleic acids and may inhibit restriction by endonucleases and other enzymatic activities.

For purposes of the instant disclosure, the following terms are defined as follows:

An amplification primer is a primer for amplification of a target sequence by hybridization and extension of the primer. For SDA, the 3' end of the amplification primer (the target binding sequence) hybridizes at the 3' end of the target sequence and comprises a recognition site for a restriction enzyme near its 5' end. The target binding sequence is generally approximately 10–20 base pairs in length. The restriction enzyme recognition site is a nucleotide sequence recognized by a restriction enzyme which will nick one strand of a DNA duplex when the recognition site is hemimodified, as described by Walker, et al. (1992a), supra. A hemimodified recognition site is a double stranded recognition site for a restriction enzyme in which one strand contains at least one derivatized nucleotide which prevents cutting of that strand by the restriction enzyme. The other strand of the hemimodified recognition site does not contain derivatized nucleotides and is nicked by the restriction enzyme. Any hemimodified restriction enzyme recognition site which is nickable by a restriction enzyme is suitable for use in SDA. Examples of the preferred hemimodified recognition sites are hemiphosphorothioated recognition sites for the restriction enzymes HincII, HindII, AvaI, NciI and Fnu4HI. Amplification primers for SDA are designated $S_1$ and $S_2$ by Walker, et al. (1992b), supra.

A "bumper" or external primer is a primer which anneals to a target sequence upstream of an amplification primer, such that extension of the external primer displaces the downstream primer and its extension product. The bumper primers therefore consist only of target binding sequences and are designed so that they anneal to the target sequence close enough to the amplification primers to displace them when extended. External primers are designated $B_1$ and $B_2$ by Walker, et al. (1992b), supra. Extension of external primers is one method for displacing the extension products of amplification primers, but heating may also be suitable in certain cases.

The terms target or target sequence refer to nucleic acid sequences (DNA and/or RNA) to be amplified. These include the original nucleic acid sequence to be amplified and its complementary second strand as well as either strand of a copy of the original target sequence produced by amplification of the target sequence.

Amplification products, extension products or amplicons are copies of the target sequence or its complementary strand produced by amplification of the target sequence.

SUMMARY OF THE INVENTION

Strand Displacement Amplification has been adapted for amplification of nucleic acid target sequences in situ in cells in suspension, on slides or in tissues, with sensitivity and specificity comparable to the in situ PCR. SDA is more gentle to the cells and tissues than is the PCR, and excellent specimen morphology is preserved. In situ amplification by SDA is compatible with immunochemical techniques, so that both amplification of target sequences and immunological staining can be performed on the same specimen. This is in contrast to the in situ PCR, in which the repeated temperature cycling may make the cellular antigens of interest undetectable by immunochemical techniques.

The instant methods for in situ SDA will generally comprise a brief fixation of the cells or tissue in a preservative which preserves the morphology of the cells, followed by addition of the reagents required for SDA. When the target sequence is DNA the cells or tissues are heated briefly prior to amplification to denature the target sequence. Heating takes place in a mixture of SDA reagents which does not include the enzymes. Upon cooling to about 37° C., the enzymes (restriction endonuclease and exo⁻ klenow) are added and the reaction is incubated at 37° C. for 30 min. to 5 hr. at about 37° C. If no prior heating is required to denature the target sequence, all of the SDA reaction components (including the enzymes) may be added directly to the fixed cells or tissues and amplification initiated as described above. After washing to remove unused primers and enzymes, the amplification products are detected by in situ hybridization of a labeled probe or by other means known in the art.

DETAILED DESCRIPTION OF THE INVENTION

Figure 1A:
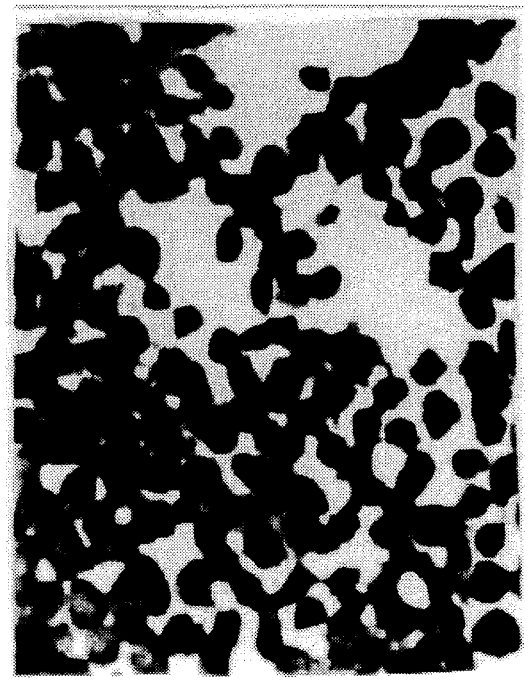
FIG. 1A and FIG. 1B illustrate the improved structural integrity and morphology of cells after in situ SDA (FIG. 1A) as compared to cells after the in situ PCR (FIG. 1B), visualized by light microscopy.

The instant methods for in situ nucleic acid amplification by SDA are based on the discovery that the solution SDA protocols described by Walker, et al. (1992a and 1992b), supra, can be performed in situ in the biochemically complex and unpredictable environment of morphologically intact cells. In general, a sample of cells (cells in suspension or tissue sections) containing nucleic acids to be amplified is first fixed briefly with a fixative which maintains the morphological integrity of the cell but does not cross-link or precipitate cellular proteins so extensively that penetration of primers and other reagents is prevented. Harsh pretreatment with protease is therefore not required after fixation to obtain penetration of primers and reagents into the fixed cells. Either cross-linking or precipitating fixatives, as are known in the art, may be used in the practice of the invention. Examples include paraformaldehyde, 4% glutaraldehyde, ethanol/acetic acid fixatives, Carnoy's fixative (acetic acid, ethanol, chloroform), 1% osmium tetraoxide, Bouin's fixative (1.21% picric acid, 11% formaldehyde, 5.6% acetic acid), Zenker's fixative (5.0% mercuric chloride, 2.5% potassium dichlorate, 5.0% acetic acid, 1.0% sodium sulfate), and acetic acid/methanol fixatives. The preferred fixative for use in the invention is 1–4% paraformaldehyde, which is preferably used to treat the cells or tissues for about 1 min. to 1 hr. It has been found that this brief fixing with paraformaldehyde allows penetration of primers and other reagents into the cells without the need for the destructive protease treatment considered essential for the in sire PCR. Fixing may be optional under certain circumstances. That is, SDA may be performed in situ in unfixed cells, especially when only RNA targets are to be amplified and no preliminary heating step is required (see below).

If a tissue section containing nucleic acids to be amplified is embedded in paraffin, the paraffin is removed prior to fixation by treatment with xylene as is known in the art. These tissue sections may have been previously fixed for other purposes (e.g., in the pathology laboratory) without regard to penetration of reagents for in situ amplification, i.e., they may have been fixed for substantially longer than 1 hr. Often, penetration of amplification reagents into the cells of the tissue section is still satisfactory in spite of extensive fixation, possibly due to the thinness of the section. However, in some cases penetration of the cells by amplification reagents may be prevented or significantly reduced by prior extensive fixation. If so, it is preferred that the tissue section be treated with protease or heat prior to in situ amplification to improve penetration of reagents into the cells of the tissue sample. Frozen tissue sections which have not been previously fixed may be fixed as described above and do not require prior protease or heat treatment.

It is an important feature of the present invention that either RNA or DNA target sequences, or both, may be amplified directly using the inventive methods. No additional steps or reagents are required to amplify RNA target sequences, unlike the in situ PCR in which reverse transcriptase must first be added to produce cDNAs which are then amplifiable in the conventional PCR protocol (G. J. Nuovo, et al. 1992. *Diag. Molec. Pathol.* 1, 98–102; G. J. Nuovo, et al. 1991. *Am. J. Pathol.* 58, 518–523; G. J. Nuovo, et al. 1991. *Am. J. Pathol.* 139, 1239–1244). The reverse transcriptase approach would also be expected to work in in situ SDA, however, and may be useful under certain circumstances.

The exo$^-$ klenow polymerase used in SDA can polymerize DNA copies of a target sequence using either RNA or DNA as the template. RNA target sequences may therefore be selectively amplified in the fixed cells or tissues by eliminating the heating step prior to initiating the SDA reaction so that only single-stranded templates are available for amplification. The double stranded DNA in the cells remains double stranded and unavailable as a template, whereas primers can hybridize to available single stranded RNA and begin specific amplification of RNA target sequences. Fixing aids in maintaining the integrity of the cells during heating. Therefore, if there is no preliminary heating step, as in RNA amplification, fixing is not needed. Unfixed cells or tissues for in situ SDA amplification may be permeabilized with detergents as is known in the art, for example, NP40, TRITON or saponin. Specific amplification of RNA target sequences may also be accomplished by treating the fixed cells or tissues with RNase-free DNase prior to initiating SDA.

Treatment of the fixed cells or tissues with RNase prior to denaturing double stranded DNA by heating degrades potential RNA target sequences and allows specific amplification of the corresponding DNA target sequences. NaOH (about 0.1M) may also be used to selectively degrade RNA and denature DNA for DNA-specific amplification.

If the heating step is included (without RNase treatment) prior to annealing of the SDA primers, both DNA and RNA target sequences will be amplified. In situ amplification of RNA by SDA is less efficient than DNA amplification, but RNA targets are generally present in the cell in greater numbers than the corresponding DNA target. The result of RNA and DNA amplification is therefore a composite of relative copy number and efficiency of amplification and is influenced by many factors. Amplification of both RNA and DNA targets is preferred for most diagnostic applications of the invention because this gives the greatest number of amplifiable target sequences per cell and, as a result, the greatest sensitivity and largest number of positive cells per sample.

If heating prior to amplification is desired, the fixed cells or tissues will generally be heated in the SDA reaction mixture minus the enzymes (0.2 mM dNTPs, 50 mM KiPO$_4$, 6 mM MgCl$_2$, 1 µg BSA, 6% DMSO, 50 nM external primers and 500 nM SDA primers). The HincII and exo$^-$ klenow polymerase enzymes are then added after the sample is removed from the heating source and allowed to cool to a temperature which is preferably optimal for enzyme activity. If the fixed cells or tissues are not to be heated, the SDA reaction mixture above including preferably about 150 units of HincII and preferably about 5 units of exo$^-$ klenow polymerase may be added to the cell sample and the amplification reaction initiated.

Amplification of the selected target sequence is essentially as described by Walker, et al. (1992a and 1992b), supra. However, in certain cases it may be advantageous to increase the concentration of reagents (especially primers) for in situ SDA to ensure that sufficient amounts enter the cells for efficient amplification. Leakage of amplicons from the cells has been a problem in in situ nucleic acid amplification methods. Such leakage is the result of the complex interaction of a variety of parameters, e.g., size of the amplicon, temperature and the degree to which the cell has been permeabilized. For this reason, a deoxyribonucleoside triphosphate (dNTP) analog comprising the dNTP conjugated to a moiety such as digoxigenin ("dig"), biotin or fluorescein isothiocyanate (FITC) may optionally be incorporated into the amplification products along with the dATPαS to facilitate retention of the amplicons within the cell and also, optionally, to serve as a tag or label to be used for detecting amplification products. Incorporation of such dNTP analogs is particularly advantageous for in situ SDA because the amplified target sequence is generally smaller than a PCR amplicon. However, even though SDA amplification products are generally smaller than PCR amplification products, it has been unexpectedly observed in the practice of the instant invention that in both cells and tissues there is less leakage associated with SDA than with PCR in situ amplification. Incorporation of dNTP analogs such as dig also has the advantage of providing an enhanced signal, as each incorporated label moiety can generate a signal by binding to anti-dig antibodies conjugated to AP (AP-α-dig).

After initiation of the reaction, the amplification of the target sequence is generally allowed to proceed at about 37° C. for about 5 min. to 2 hr., preferably 30 min. to 1 hr. It has been discovered that the time required for in situ amplification by SDA is significantly less than the time required to obtain a comparable level of target amplification in situ by the PCR.

Following target amplification, the amplicons produced may be detected by any of several methods known in the art for detection of specific nucleic acid sequences. For example, amplification products may be detected in the cell or tissue by specific hybridization to an oligonucleotide detector probe. The oligonucleotide probe is a short oligonucleotide which includes a detectable label, i.e., a moiety which generates or can be made to generate a detectable signal. The label may be incorporated into the oligonucleotide probe by nick translation, end-labeling or during chemical synthesis of the probe. Many directly and indirectly detectable labels are known in the art for use with oligonucleotide probes. Directly detectable labels include those labels which do not require further reaction to be made detectable, e.g., radioisotopes, fluorescent moieties and dyes. Fluorescent labels such as fluorescein isothiocyanate (FITC) or radioisotopes such as $^{32}$P, $^{33}$P, $^{125}$I or $^{35}$S are preferred for use in labeling probes for directly detecting in situ amplified target sequences in the present invention. Indirectly detectable labels include those labels which must be reacted with additional reagents to be made detectable, e.g., enzymes capable of producing a colored reaction product, biotin, avidin, digoxigenin, antigens, haptens or fluorochromes. The signal from enzyme labels is generally developed by reacting the enzyme with its substrate and any additional reagents required to generate a colored, insoluble, enzymatic reaction product. Biotin (or avidin) labels may be detected by binding to labeled avidin (or labeled biotin) or labeled anti-biotin (or labeled anti-avidin) antibodies. Digoxigenin and hapten labels are usually detected by specific binding to a labeled anti-digoxigenin (anti-dig) or anti-hapten antibody. Enzymes are preferred for use as indirectly detectable labels in the present invention. Most preferred is alkaline phosphatase (AP) because it is stable and has been used extensively for labeling in tissues and cells. The presence of AP may be detected by reaction with a substrate. The preferred substrates for detection of AP are Vector Red/Vector Blue (Vector Labs, CA), 5-bromo-4-chloro-3-indolyl phosphate (BCIP)/nitro blue tetrazolium (NBT) (Sigma Chemical Company, St. Louis, Mo.) or Nuclear Fast Red (Sigma Chemical Company). Vector Red has the added advantage of fluorescence, allowing visualization of a positive signal either by conventional light microscopy or by fluorescence microscopy. Methods for developing the colored reaction product of AP with these substrates are known in the art.

To detect amplified target sequences by in situ hybridization to a labeled probe, the cells or tissues are exposed to the labeled probe under reaction conditions appropriate for specific hybridization of the probe to the single stranded amplification products. In general, the labeled probe will be selected such that it hybridizes to a nucleotide sequence in the amplicon which is between the binding sites of the two amplification primers. However, a labeled probe may also have the same nucleotide sequence as either of the amplification primers. The preferred methods for detection of the in situ amplification products by hybridization to a detector probe are the in situ hybridization methods described by J. B. Lawrence, et at. (1989. Cell 57, 493–502), J. B. Lawrence, et at. (1990. Proc. Natl. Acad. Sci. USA 87, 5420–5424) and in U.S. Pat. No. 4,888,278. These disclosures are hereby incorporated by reference.

Alternatively, amplified target sequences may be detected in situ by primer extension as described by Walker, et at. (1992b), supra. In the primer extension method an oligonucleotide primer comprising a detectable label is hybridized in situ to the amplified target sequences and extended to a diagnostic length at 37° C. by addition of polymerase. For detection the primer may be 5' end-labeled, most preferably using $^{32}$P. Alternatively, extension of the hybridized primer may incorporate a dNTP analog comprising a directly or indirectly detectable label. For example, extension of the primer may incorporate a dig-derivatized dNTP, which is then detected after extension by reaction with AP-α-dig and a suitable AP substrate. The primer to be extended may either be the same as an amplification primer or it may be a different primer which hybridizes to a nucleotide sequence in the amplicon which is between the binding sites of the amplification primers.

The detectable label may also be incorporated directly into the amplicons during target sequence amplification. For example, one of the dNTP s in the conventional SDA reaction may be completely or partially replaced with a dNTP analog which comprises a dNTP conjugated to a directly or indirectly detectable label. For example, dUTP conjugated to the desired label may be substituted for dTTP in the SDA reaction. The polymerase then incorporates the label directly into the amplification products generated by the reaction. The label may be directly or indirectly detectable. Preferably, the label conjugated to the dNTP is a fluorescent label which may be detected directly in the amplicons by fluorescence microscopy or flow cytometry. In an alternative preferred embodiment, the label conjugated to the dNTP is biotin or digoxigenin, which may be detected by reaction with streptavidin/FITC and fluorescence microscopy or flow cytometry.

The label of the hybridized detector probe, the label of the extended primer or the label incorporated into the amplification products is then detected as an indication of the presence of amplified target sequences in the cells. This may require the addition of reagents to the cells to develop the signal of an indirectly detectable label such as AP, biotin or dig. Microscopic analysis of the cells is preferred when the detectable label is an enzyme. Microscopic analysis may be either by visual observation of the cells or tissues (fluorescence or light microscopy), or automated image analysis using instruments such as DISCOVERY (Becton Dickinson Image Cytometry, Leiden, Holland) to evaluate the number and signal intensity of positive cells. Alternatively, amplification products may be released from cells and visualized after gel electrophoresis as bands of amplification products, e.g., by EtBr staining, hybridization of a detector probe or primer extension. When a radiolabel is used for the primer or detector probe, amplification products may be visualized by autoradiography of the gels. Use of a directly detectable fluorescent label allows fluorescence analysis of cells in suspension by flow cytometry (e.g., FACSCAN, Becton Dickinson Immunocytometry Systems, San Jose, Calif.). A shift in peak fluorescence to the right on a plot of cell number vs. fluorescence intensity is indicative of an increased number of cells containing the target sequence. Conversely, a shift in peak fluorescence to the left on the plot is indicative of a reduced number of cells containing the target sequence.

Heat induces autofluorescence of the cells being analyzed and has presented problems in detection of the products of in situ amplification by flow cytometry. At least some of the increased autofluorescence seen in cells after PCR is likely to be induced by temperature cycling. While autofluorescence was found to be reduced for flow cytometric analysis after in situ SDA as compared to the in situ PCR, further modifications to the SDA protocol were required to optimize data analysis. Of particular relevance was the discovery that monocytes non-specifically take up detector probes and thereby increase non-specific fluorescence. It was found that such non-specific fluorescence could be reduced by increasing the DMSO to 10 μL from the 6 μL which had been customary. It was also found that direct incorporation of a label by primer extension in many cases gave better separation of fluorescence peaks than detection of amplification products by in situ hybridization to a detector probe.

The present inventive methods for in situ amplification and detection of target nucleic acid sequences are particularly useful for detection and analysis of HIV-1 infected lymphoid cells. Recent publications demonstrate that the number of HIV-1 infected cells is greater in lymphoid tissue than previously believed and is significantly higher than in peripheral blood (G. Pantaleo, et al. 1991. *Proc. Nat. Acad. Sci. USA* 88, 9838–9842; S. Jurriaans, et al. 1992. *AIDS* 6, 635–641 ). This discovery suggests that, even when the viral load is low (as it is early in infection), the lymphoid organs may serve as a reservoir for the virus. The unexpectedly large numbers of HIV-1 positive cells in lymphoid tissues also suggests that after destruction of follicular dendritic cells (FDC) and the architecture of the lymph node, HIV-infected cells are released into the circulation. This may occur only at later stages of the disease. Limiting detection to peripheral blood mononuclear cells (PBMC) may therefore not reflect the site of highest viral concentration in vivo. Further, even when viral load in PBMC is low, active viral replication has been shown in lymphoid tissues, raising questions about the concept of clinical latency (G. Pantaleo, et al. 1993. *Nature* 362, 355–358; J. Embretson, et al. 1993. *Nature* 362, 359–362). The sensitivity and specificity of in situ SDA may therefore allow very early detection of HIV-1 in lymphoid tissue, prior to the appearance of HIV-1 positive cells in the peripheral blood.

The present invention for the first time provides means for Strand Displacement Amplification of nucleic acids in situ in cells on slides, in suspension and in tissues. PCR amplification procedures have also been reported for use in situ. The amplification efficiency for in situ SDA is approximately the same as that reported for the in situ PCR (i.e., $10^9$). However, in Mtu SDA provides certain unexpected advantages over the in situ PCR. Because it does not require multiple rounds of temperature cycling to achieve amplification of the target, in situ SDA is more gentle to the cells and tissues. Hence, this method is more consistent with procedures in which single cell analysis is important. After repeated cycling at 95° C. in the PCR, the morphology and aspect of the cells and tissues appears damaged. The cells tend to aggregate and leak their contents into the medium, making detection and quantitation of the number of positive cells difficult, as the enzymatic substrate overlaps more than one positive cell. Tissues lose structural definition as well. In addition, double staining procedures involving sequential in situ hybridization and immunocytochemistry can be virtually impossible after the in situ PCR because temperature cycling may destroy the antigenic site of interest. SDA, in contrast, allows such double staining and thus permits a better and more complete analysis of the cells.

When a cells in suspension or in tissues are to be analyzed both by in situ SDA and immunostaining, it is preferred that binding of the antibody to the epitope or antigen of interest be done prior to fixation and that the antibody be conjugated to an indirectly detectable label, e.g., biotin. The antibody-conjugate is then stabilized on the cells by fixation. After in situ SDA, the bound antibody is detected by reaction with appropriate signal developing reagents, e.g., streptavidin conjugated to a fluorochrome.

Detection of RNA by the PCR requires use of an additional enzyme (i.e., reverse transcriptase) to transcribe the single stranded RNA template into a cDNA copy which will serve as a template for subsequent PCR amplification. The exo$^-$ klenow DNA polymerase used in Strand Displacement Amplification, however, has now been shown to use single stranded RNA as a template as well as DNA. This single procedure therefore allows amplification and detection of RNA and/or DNA simply by selection of the pre-amplification treatment of the target (ie., denaturation, no denaturation, DNase or RNase). The present invention for the first time provides a means for performing nucleic acid amplification in situ under physiological conditions (i.e., without fixation), as described above. This feature gives in situ SDA a particular advantage over the in situ PCR, as rapid detection and quantitation of RNA and DNA within a cell will be useful for assessing drug therapy and monitoring viral load in patients. The instant methods for in situ SDA amplification and detection also make it possible to distinguish HIV-infected cells which support active viral replication (RNA) from those which are in a latent stage (DNA only). This is important for diagnosis, as it has been shown that RNA levels correlate better to the patient's clinical status than DNA levels and are a more reliable indicator of viral load (J. Genesca, et al. 1990. *J. Infect. Dis.* 162, 1025–1030). It is also highly desirable to be able to identify the infected cell type by morphological or cytochemical techniques, as is only possible using in situ SDA amplification and detection methods.

The following experimental examples are provided to illustrate certain embodiments of the invention, but are not to be construed as limiting the invention as defined by the appended claims.

EXAMPLE 1

SDA and the PCR were first performed in suspension in the conventional manner on nucleic acids extracted from tissues and cells. This served to confirm, prior to performing in situ SDA, which tissues were positive for HIV-1 and which were negative, thereby providing a basis for interpretation of the results of in situ SDA amplifications.

SDA and the PCR were then performed in situ directly on sectioned lymph node tissue samples from patients determined to be positive or negative for HIV-1 by serology. Both amplification methods were performed on the same tissue sample to minimize variability. The tissues were removed from the slides using a clean scalpel and were washed in 1 ml of xylene for 2 min. to remove the paraffin. The samples were then centrifuged in a microfuge at 1200 rpm, the xylene was pipetted out and the tissue was washed twice with 1 ml of 100% ethanol before being dried at 55° C. DNA was also solubilized from HIV-positive cell lines (ACH2 and 8E5) and HIV-negative cell lines (CEM and A301) by disrupting and phenol-extracting the cells using methods known in the art. The DNAs from the positive and negative cell lines were used as controls. Oligonucleotide primers and probes were synthesized on an Applied Biosystems, Inc. 380B DNA synthesizer. The probes were synthesized with a modified AMINOLINK (Glen Research, Sterling, Va.) at their 5' end to allow labeling with alkaline phosphatase. Alternatively, in some cases the primers and probes were end-labeled with digoxigenin using a commercial kit (Boehringer-Mannheim). The nucleotide positions in the HIV genome of the following primers and probes are numbered according to the sequence of human immunodeficiency virus HXB-2 (GENBANK Accession Number K03455).

The PCR was performed essentially as previously described by O. Bagasra (1992. *New Engl. J. Med.* 326, 1385–1391). Each PCR contained the prepared tissue, 500 ng of each amplification primer, 0.2 mM dNTPs, 1.5 mM MgCl$_2$ and 1 unit Taq polymerase (Promega) in the buffer supplied by the manufacturer. The target sequence for amplification was in the HIV gag gene. The sequences of the primers were as follows: SK38 (nucleotides 1541–1578) ATAATCCACCTATCCCAGTAGGAGAAT (SEQ ID NO:1) and SK39 (nucleotides 1657–1630) TTTGGTCCTTGTCTTATGTCCAGAATGC (SEQ ID NO:2). Cycling was performed for 30 cycles (94° C. for 45 sec., 55° C. for 45 sec., 72° C. for 45 sec.), followed by a final extension at 72° C. for 5 min. Aliquots (10 µl) of the reaction were then denatured at 95° C. for 2 min. and incubated for 60 min. with 2 pmol of probe SK19 (nucleotides 1595–1635) ATCCTGGGATTAAATAAAATAGTAAGAATGTATAGCCTAC (SEQ ID NO:3) end-labeled with $^{32}$P and T4 kinase. This probe hybridizes to an internal segment of the amplified sequence. The resulting amplification products hybridized to the labeled probe were analyzed on a gradient gel (10–20% PAGE) and autoradiographed. Amplification products were also directly detected on the gel by staining with ethidium bromide (EtBr). The total time required for in situ PCR amplification was approximately 4 hrs.

SDA was performed essentially as described by Walker, et al. (1992b), supra. Each SDA reaction contained 150 units of HincII (New England Biolabs, 75 u/µl), 5 units of exo$^-$ klenow polymerase (United States Biochemicals), 0.2 mM dNTPs (dCTP, dGTP, dTTP and dATPαS—Pharmacia), 50 mM KiPO$_4$, 6 mM MgCl$_2$, 1 µg BSA, 6% DMSO, 50 nM external primers B$_1$ and B$_2$), 500 nM amplification primers (S$_1$ and S$_2$), and the prepared tissue. SK38 and SK39 (SEQ ID NO:1 and SEQ ID NO:2) were used as the external primers for SDA. The sequences of the amplification primers were AATAGTCGCTTACTTGTTGACGGATAATCCTGGG ($S_1$, SEQ ID NO:4) and AAGTAACCGACTATTGTTGACGGCTATACATTCT ($S_2$, SEQ ID NO:5). The amplification primers corresponded to nucleotide position numbers 1582–1594 and 1623–1611, respectively.

The SDA samples (minus the enzymes) were incubated at 95° C. for 2–3 min. followed by an incubation at 37° C. for 2 min. The enzymes were then added and the incubation continued for 2 hr. at 37° C. An aliquot (10 μl) of the reaction was then mixed with 1 gM of an internal probe (ACTATTT-TATTTAAACC, SEQ ID NO:6) end-labeled with $^{32}$P and T4 kinase. After incubation at 95° C. for 2 min., followed by 2 min. at 37° C., the probe was extended by addition of 2 units of klenow polymerase (Promega) for 15–30 min. at 37° C. The products were then mixed with loading buffer and analyzed by gel electrophoresis on a 15% urea polyacrylamide gel. The gel was dried and autoradiographed. In some cases, for both the PCR and SDA, a radiolabelled dNTP (e.g., $dCTP^{32}$) was included in the reaction mixture and the labelled amplification products were detected directly on autoradiographs after electrophoresis and drying of the gel. The total time required for in situ SDA amplification was approximately 2 hrs.

After the PCR, ethidium bromide staining of the gel showed a clearly positive amplified product in two patients and three negative patients in the first group. The bands visualized were of the predicted size for the amplification products of the HIV-1 target sequence and migrated at the same position as the amplified product of the positive cell line. No signal was seen after amplification of the negative cell line or when the primers or the enzyme (Taq) were omitted from the reaction mixture. Hybridization in solution of the PCR amplification products to the $^{32}$P-labeled internal probe SK19 (SEQ ID NO:3) confirmed the two positive and the three negative patients in this group. In a second group of patients, strongly positive bands of amplified HIV-1 target sequence were seen in three of six patients on ethidium bromide staining. A very faint band was seen in one patient in this group. Solution hybridization of the amplification products of this patient with the labeled internal probe showed that the faint band was actually a clearly positive band. No amplification was detected from serologically negative patients. Seronegative patients included some with adenocarcinoma, carcinoma, breast cancer and cervical lymphadenopathy.

Both ethidium bromide staining of 10% polyacrylamide gels and autoradiography after SDA amplification revealed amplification only in HIV-infected cells. All six seropositive patient samples in the first group tested had clear bands indicating amplified products and corresponding to the bands found in the amplification of the two positive cell lines. No signal was detected in the negative cell line. Autoradiographs after hybridization and extension of a $^{32}$P-labeled probe confirmed the six positive patients with amplification products migrating at the same position as the amplified products from the positive cell line. These results were confirmed by analysis of the SDA amplification products from eighteen additional seropositive patients on autoradiographs.

Paraffin embedded tissue sections from HIV-1 positive patients were also observed microscopically after the in situ PCR and in situ SDA. Comparisons were made between 1) in situ hybridization after in situ amplification by SDA, and 2) in situ hybridization without prior nucleic acid amplification. In both cases there was a strong signal, but more cells were determined to be positive after in situ SDA than by conventional in situ hybridization. In each case, the morphology of the tissue was well preserved and the loss of morphological detail was minimal. In contrast, the in situ PCR resulted in a significant loss of morphological detail and deterioration of tissue structure.

Figure 1B:
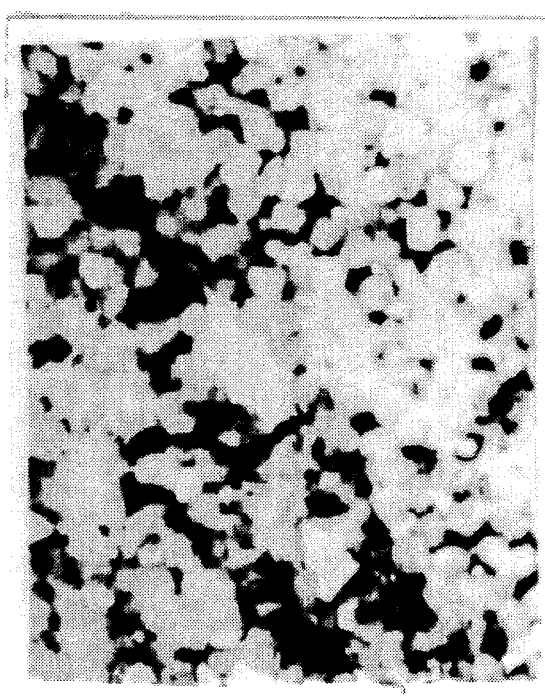

FIGS. 1A and 1B are light microscopic analyses showing a comparison between in situ PCR and in situ SDA performed on H9 cells. In situ PCR resulted in clear damage to the cells (FIG. 1A), whereas in sire SDA left significantly more cells morphologically intact and the positive cells more easily identifiable (FIG. 1B). SDA-treated cells were indistinguishable from untreated cells Specifically, staining after PCR was non-homogeneous and irregular, the nuclei of the cells were not visible, debris surrounded the cells and cells were lost from the slides. In situ SDA performed on a tissue section from an HIV negative patient showed no apparent signal on microscopic examination and the morphology of the tissue was well preserved, demonstrating that in situ SDA is not only highly sensitive but highly specific for HIV-positive cells.

EXAMPLE 2

This experiment illustrates 1 ) in situ SDA of single stranded targets (DNA and RNA) with initial denaturation, and 2) in situ SDA without initial denaturation to restrict amplification to pre-existing single stranded species (RNA). Tissue sections on slides (lymph nodes, spleen and brain from HIV-1 positive patients) were deparaffinized in xylene, passed through graded ethanol (100%–70%) and fixed in 4% paraformaldehyde/phosphate buffered saline (PBS) for 10 min. at room temperature. The tissues were rehydrated in PBS/5 mM $MgCl_2$ for 5 min. An aliquot of the SDA reaction mixture (see Example 1 ) was added and the slides were incubated for 3 min. on a heating block at 95° C. Slides for RNA amplification were not heated. The HincII restriction endonuclease and exo$^-$ Klenow were added under a coverslip and the incubation was continued for 2 hr. at 37° C. in a humidified chamber. The slides were washed in 1X SSC, incubated for 10 min. in 95% formamide/0.2X SSC at 70° C. and rinsed in ice cold 0.1X SSC. An internal SDA probe (20–50 ng, SEQ ID NO:3 labeled with alkaline phosphatase as described by H. Kiyama, et al. (1991. *J. Histochem. Cytochem.* 39, 1371–1384) and M. A. Farquharson, et al. (1992. *Am. J. Clin. Pathol.* 45, 1999–1002) was added under the coverslip and incubated for 60 min. at 55° C. After washing in 1X SSC at 45° C., alkaline phosphatase was detected using either Vector Red or Fast Red substrate according to the manufacturer's instructions. The slides were counterstained with Methyl Green, coverslipped with permanent mounting and analyzed by light microscopy and/or DISCOVERY image analysis. In some cases, a modified dNTP (e.g., dig-dUTP from Boehringer-Mannheim) was included in the reaction mixture and the amplification products were detected using a suitable dilution of an anti-dig-antibody labeled with alkaline phosphatase. Alkaline phosphatase was detected with Vector Red or Fast Red as above.

SDA amplification products within the cells of the tissues were detected by light microscopy, verifying that DNA could be amplified in situ after denaturation of the template DNA as is customary for solution SDA. SDA amplification products were also detected within the cells of the tissues in which the templates had not been initially denatured, indicating that RNA could also be amplified in situ by SDA when the denaturation step was omitted. In situ SDA was also performed on cells in suspension using the cell lines ACH2 and CEM with the same reaction conditions as described for tissues. Similar results were obtained for in situ SDA of target sequences in cells in suspension. Detection of the amplified products in cells in suspension was done by in situ hybridization using either an oligonucleotide probe labeled with alkaline phosphatase and detected with BCIP/NBT or an oligonucleotide probe labeled with FITC and detected by fluorescence. In some cases, the incorporation of a modified dNTP (e.g., dig-UTP) during the SDA reaction was detected with an alkaline-phosphatase-labeled anti-dig-antibody detected by incubation with the BCIP/NBT substrate. After counterstaining, the slides were analyzed by light microscopy and/or using the DISCOVERY image analyzer.

A series of in situ SDA reactions using different preamplification sample treatments was performed on slides prepared from a single HIV-1 positive patient—1) in situ hybridization without prior amplification, 2) in situ SDA of DNA and RNA (denatured), 3) in situ SDA of RNA (not denatured), 4) in situ SDA of DNA (RNase treatment—1 mg/ml for 30 min. at 37° C.) and 5) in situ SDA of RNA (DNase treatment—150 units/ml for 30 min. at 37° C.). To quantitate the level of signal, slides were analyzed with the DISCOVERY computerized automatic image analyzer. The image analyzer captures the data, assigns values to the parameters and evaluates and manipulates the data. Each positive event is analyzed at high magnification for morphological parameters and the data is stored with a subimage of the selected object on a 100×100 pixel roster. Data can be displayed in list, histogram or scatterplot form. The system quantitates the number of positive cells per field and also measures the amount of signal.

Figure 2:
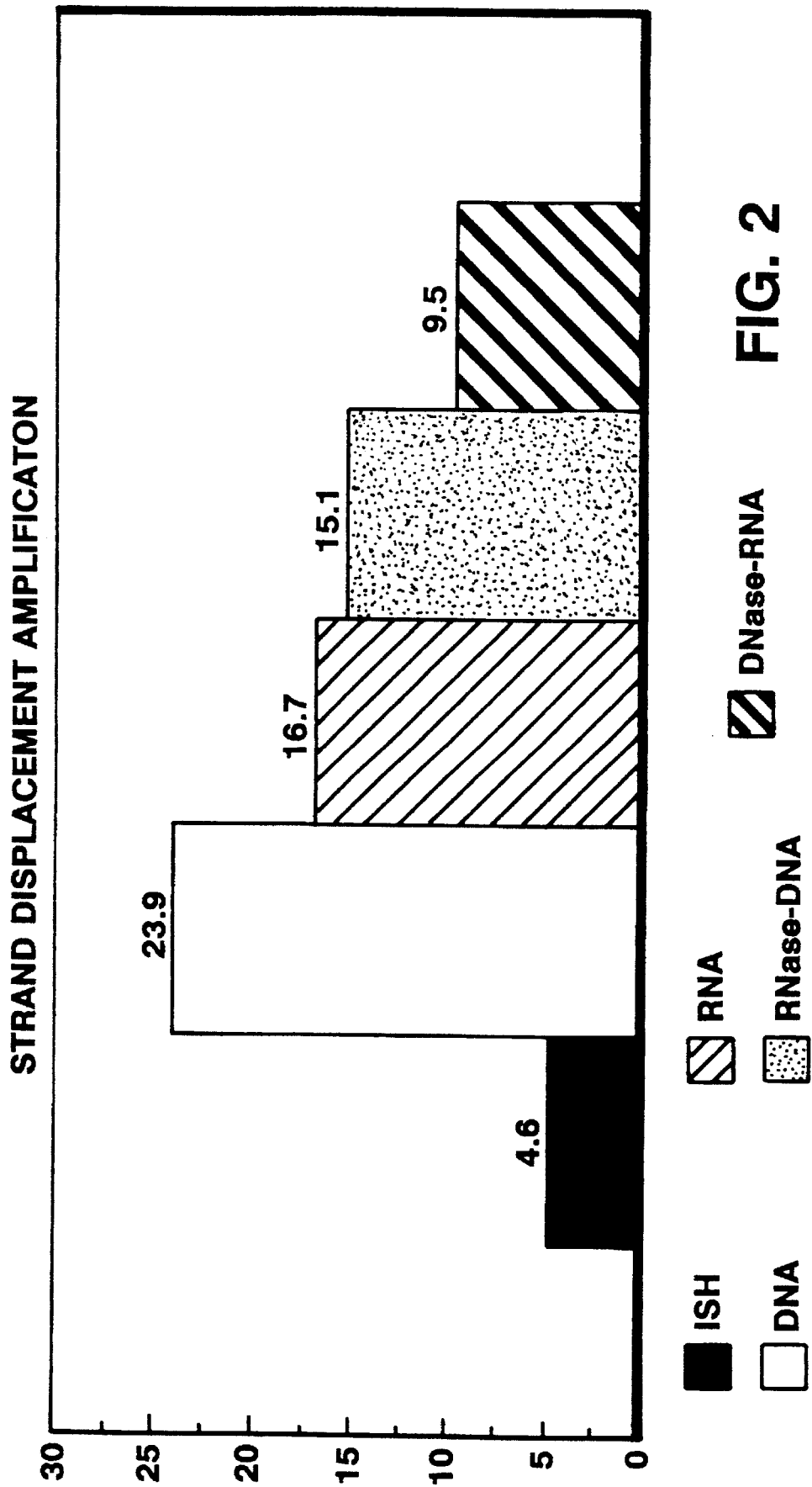
FIG. 2 is a histogram showing the relative percentages of positive cells detected by DISCOVERY analysis after in situ SDA of both DNA and RNA targets (DNA), RNA targets without prior heat denaturation (RNA), RNA targets after treatment with DNase (DNase-RNA), and DNA targets after treatment with RNase (RNase-DNA).

The results are shown in histogram form in FIG. 2. In situ hybridization alone (ISH) identified 4.6% positive cells, SDA of both DNA and RNA (DNA) identified 23.9% positive cells, SDA of RNA (RNA) identified 16.7% positive cells, SDA of DNA (RNase) identified 15.1% positive cells and SDA of RNA (DNase) identified 9.5% positive cells. SDA clearly occurred under all reaction conditions, but the maximum amount of positive signal is about sixfold higher after amplification. Further, these results demonstrate that in situ SDA can be made selective for DNA or RNA or both simply by manipulation of the reaction conditions prior to initiating the amplification reaction. Direct comparison with amplification by in situ PCR was impossible because after cycling for 30 cycles at high temperatures, the morphology of the tissues was virtually destroyed and the analysis was equivocal. This demonstrates that in situ SDA with its milder temperature conditions provides significantly better results than the in situ PCR on amplification of nucleic acids in tissues and cells in suspension.

EXAMPLE 3

8E5 cells were harvested and adjusted to approximately $10^6$ cells/mL. The cells were pelleted by centrifugation and washed with 10 mL of PBS buffer, centrifuging at 1000 rpm for 10 min. to recover the cells. The washed cells were then fixed in 4% paraformaldehyde in PBS for 20 min. at room temperature, pelleted at 1500 rpm for 5 min. and washed as before with 10 mL PBS buffer. The cells were counted, adjusted to $5 \times 10^5$ cells per sample to be analyzed and transferred to small, clear 0.5 mL tubes coated with 25 mg/mL acetylated BSA for 10–20 min. The cells were then pelleted and resuspended in 92 µL of SDA mixture (10 µL of 0.5M $KiPO_4$, 1 µL of 10 mg/mL BSA, 10 µL of 100% DMSO, 2 µL of 10 mM mixed dNTPs, 1 µL each of 100 ng/µL primers $B_1$ and $B_2$, 1 µL each of 10 ng/µL primers $S_1$ and $S_2$, 24 µL of 25 mM $MgCl_2$, 2 µL 55% glycerol and 39 µL water). When the amplification products were labeled by direct incorporation of a detectable label, dUTP-FITC was partially substituted for dTTP in the SDA reaction. The amplification primers were as in Example 1.

The prepared tubes were placed into a 95° C. thermoblock for 3 min. and transferred to a 37° C. water bath for an additional 3 min. During the 37° C. incubation the enzyme mixture was prepared (about 150 units/reaction HincII and about 5 units/reaction exo$^-$ klenow). The enzyzme mixture (3 µL) was then added to each tube and mixed well. No enzymes were added to negative control samples. The samples were incubated at 37° C. in a water bath for about 2–3 hrs. Following amplification, the cells were pelleted in an EPPENDORF microcentrifuge for 2 min. at 5000 rpm. 75 µL of the supernatant was removed for agarose gel electrophoresis to analyze the extent of amplicon leakage from the cells.

For detection of amplification products by in situ hybridization, the amplification products in the cells were hybridized in 25 µL of SDA mix to 75 ng of SEQ ID NO:3 conjugated to FITC at 95° C. for 5 min. followed by 56° C. for 1 hr. The cells were then washed once in 2X SSC, 500 µg/mL BSA at 37° C. for 30 min. and once in 1X SSC, 500 µg/mL BSA at 37° C. for 30 min. The cells were resuspended in PBS prior to detection of fluorescence by flow cytometry. Fluorescence was detected and quantitated using a FACSCAN flow cytometer (Becton Dickinson Immunocytometry Systems, San Jose, Calif.), acquiring light scatter and fluorescence data in LYSIS II software (Becton Dickinson Immunocytometry Systems).

Figure 3A:
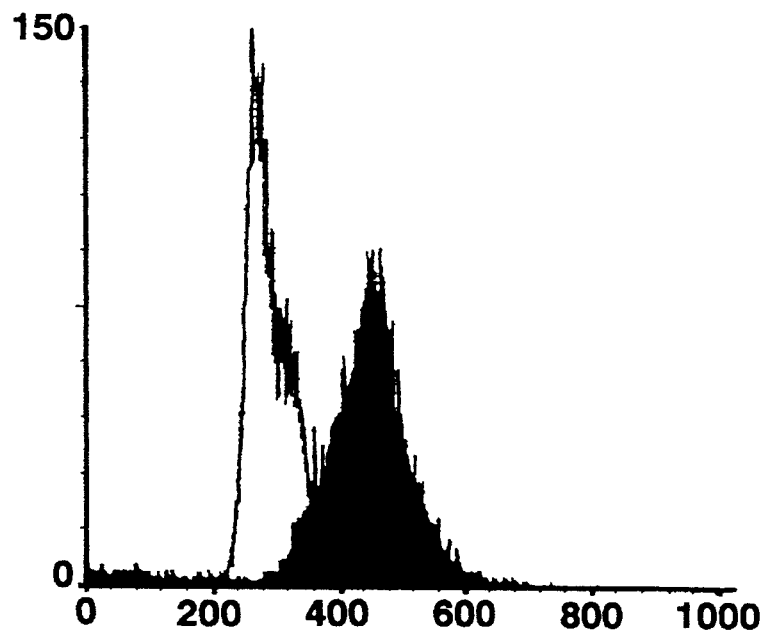
FIG. 3A is a plot of cell number vs. fluorescence showing the peak shift indicating positive in situ amplification of target sequences. The shaded peak corresponds to amplification in the presence of enzymes and the open peak corresponds to amplification minus enzymes. Amplification products were detected by in situ hybridization.
Figure 3B:
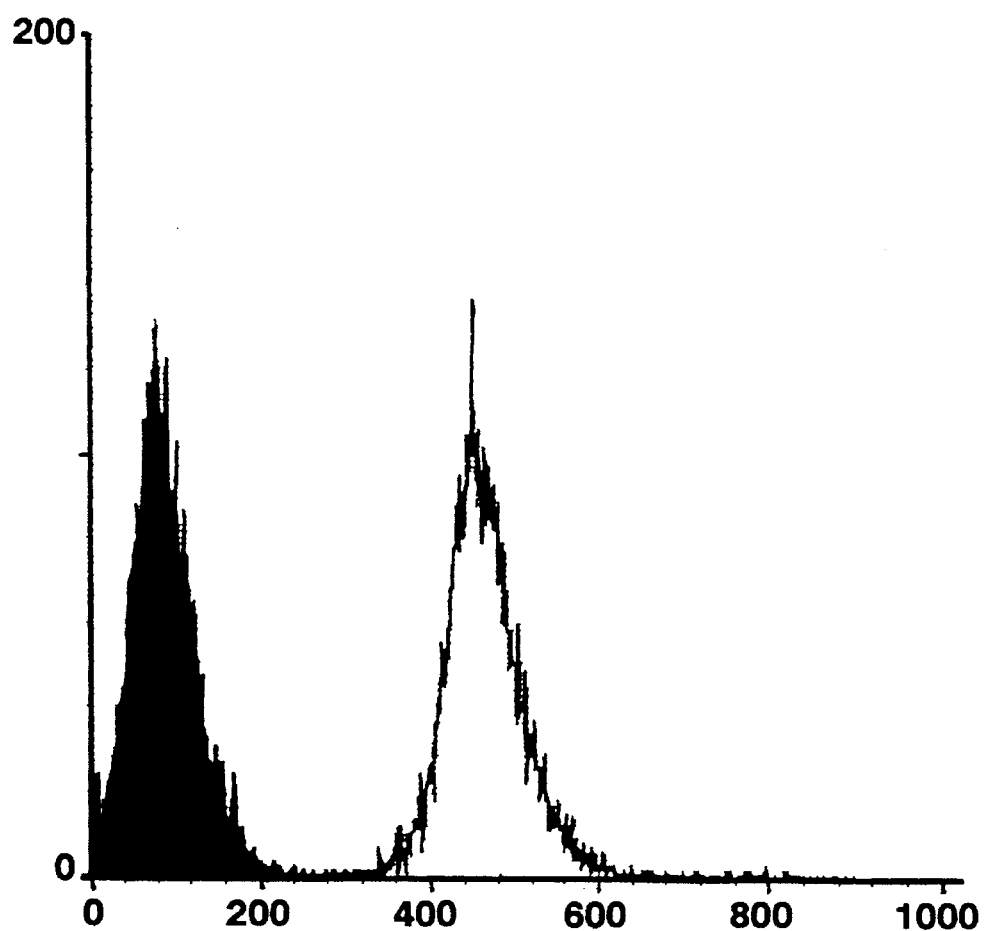
FIG. 3B shows improved peak separation when amplification products were detected by direct incorporation of a fluorescent label during amplification (open peak=amplification plus enzymes, shaded peak=amplification minus enzymes).
Figure 4A:
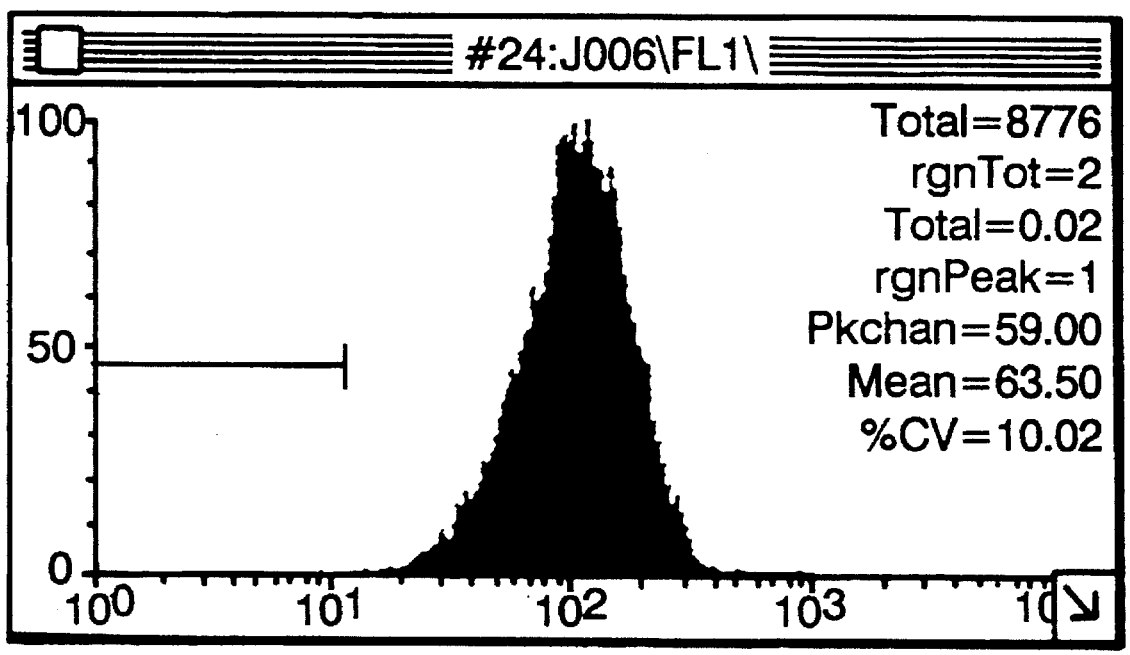
FIG. 4A is a plot of cell number vs. fluorescence for AC4 cells after in situ amplification.

In cells analyzed by hybridization of a detector probe, logarithmic plots of cell number vs. fluorescence showed an approximately 6-fold shift to the fight in the peak fluorescence signal in positive cells as compared to the negative control (FIG. 3). Direct incorporation of the fluorescent label gave improved separation between the peaks for positive and negative samples (FIG. 4), an approximately 15-fold difference. These data demonstrate that flow cytometry can be used in combination with in situ nucleic acid amplification for detection and quantitification of amplified target sequences within cells.

Figure 4B:
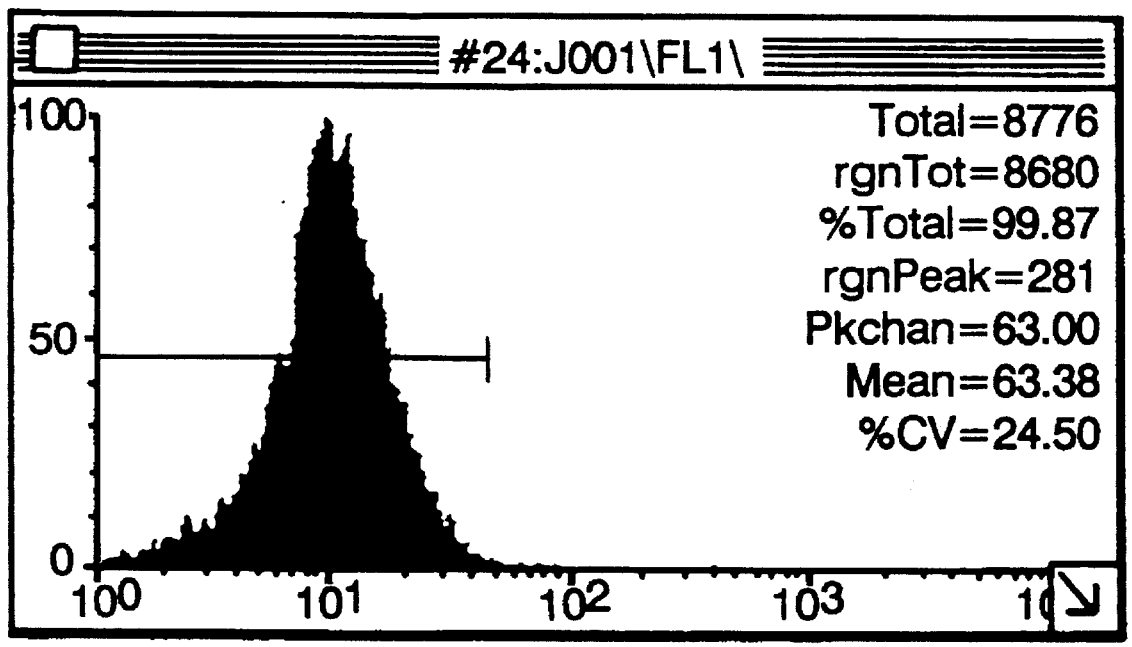
FIG. 4B is a similar plot for A301 cells.

Similar experiments were performed using A301 cells (negative for HIV) and ACH2 cells (positive for HIV). In situ SDA was allowed to proceed for 2 hr. at 37° C. A biotin label was incorporated into the amplification products during amplification via a dUTP-biotin conjugate and detected by reaction with streptavidin conjugated to FITC. Log plots of cell number vs. fluorescence showed an approximately one log increase in fluorescence in the HIV-positive cells (FIG. 4A) as compared to the negative cell line (FIG. 4B).

What is claimed is:

1. A method for in situ strand displacement amplification of a target sequence comprising the steps of:
   a) providing a sample of nonliving cells in which the morphological integrity of the cells is maintained and reagents for use in the amplification, including primers, deoxynucleoside triphosphates, an exonuclease deficient polymerase, and a restriction endonuclease, can penetrate the cells;
   b) within the cells, hybridizing an amplification primer 3' to the target sequence, the amplification primer comprising a restriction enzyme recognition site 5' to a target binding sequence, and hybridizing an external primer 5' to the amplification primer;
   c) extending the amplification primer and the external primer in the presence of the exonuclease deficient polymerase and four deoxynucleoside triphosphates, at least one of which is an α-thio deoxynucleoside triphosphate, to produce an amplification primer extension product which is displaced from the target sequence by the extension of the external primer;
   d) in the presence of the exonuclease deficient polymerase and deoxynucleoside triphosphates, making the displaced amplification primer extension product double stranded by synthesizing a complementary strand
   e) nicking one strand of the double stranded primer extension product at the restriction enzyme recognition site which recognition site includes the α-thio deoxyribonucleoside triphosphate using the restriction endonuclease;
   f) using the strand complementary to the nicked strand as a template, polymerizing a strand from the 3' end produced by the nick with the exonuclease deficient polymerase and the deoxynucleoside triphosphates, whereby the nicked strand is displaced from the template strand; and
   g) repeating steps e) and f), whereby the target sequence is amplified in situ.

2. The method of claim 1 wherein the restriction endonuclease is HincII.

3. The method of claim 1 further comprising detecting the amplified target sequence.

4. The method of claim 3 wherein the sample of nonliving cells is selected from the group consisting of cells in suspension and tissue sections.

5. The method of claim 3 wherein the amplified target sequence is detected by in situ hybridization to a detector probe comprising a detectable label.

6. The method of claim 3 wherein the amplified target sequence is detected by hybridizing a primer to the amplified target sequence and extending the primer with a DNA polymerase to synthesize a sequence complementary to the amplified target sequence, wherein the hybridized primer comprises a detectable label, or a detectable label is incorporated into the complementary sequence by incorporating nucleotides comprising a detectable label.

7. The method of claim 6 wherein the primer is 5' end-labeled with $^{32}P$.

8. The method of claim 3 wherein the amplified target sequence is detected by means of exonuclease deficient polymerase incorporation of nucleotides comprising a detectable label into the amplified target sequence.

9. The method of claim 8 wherein the detectable label is selected from the group consisting of fluorescent labels, digoxigenin and biotin.

10. The method of claim 6 or 8 wherein the amplified target sequence is detected by means of a fluorescent label.

11. The method of claim 10 wherein the amplified target sequence is detected by flow cytometry.

12. The method of claim 6 or 8 wherein the amplified target sequence is detected by automated image cytometry.

13. The method of claim 6 or 8 wherein the amplified target sequence is detected by means of a detectable label comprising alkaline phosphate.

14. The method of claim 13 wherein the amplified target sequence is detected by flow cytometry.

15. The method of claim 3 wherein amplification of a DNA target sequence is detected.

16. The method of claim 3 wherein amplification of an RNA target sequence is detected.

17. The method of claim 15 wherein amplification of an HIV target sequence is detected.

18. The method of claim 16 wherein amplification of an HIV target sequence is detected.

19. A method for in situ strand displacement amplification of a double stranded target sequence comprising the steps of:

a) providing a sample of nonliving cells in which the morphological integrity of the cells is maintained and reagents for use in the amplification, including primers, deoxynucleoside triphosphates, an exonuclease deficient polymerase, and a restriction endonuclease, can penetrate the cells;

b) within the cells, hybridizing two amplification primers comprising restriction endonuclease recognition sites near their 5' ends to opposite nucleic acid strands flanking the target sequence and hybridizing two external primers to opposite strands of the target sequence 5' to the amplification primers;

c) extending the amplification primers and the external primers in the presence of four deoxynucleoside triphosphates, at least one of which is an α-thio deoxynucleoside triphosphate, to produce first extension products of both amplification primers, the extension products being displaced from the target sequence by the extension of the external primers;

d) hybridizing the amplification primers and the external primers to the amplification primer extension products and extending the amplification primers and external primers in the presence of the deoxynucleoside triphosphates, whereby extension of the external primers displaces a second extension product of each of the amplification primers;

e) making the displaced second extension products double stranded by synthesizing a complementary strand in the presence of the exonuclease deficient polymerase and the deoxynucleoside triphosphates;

f) nicking one strand of each of the double stranded second extension products at the restriction enzyme recognition site, which includes the α-thio deoxyribonucleoside triphosphate, with the restriction endonuclease;

g) using the strand complementary to the nicked strand as a template, polymerizing a strand from the 3' end produced by the nick in the presence of the deoxynucleoside triphosphates using the exonuclease deficient polymerase whereby the nicked strand is displaced from the template strand; and h) repeating steps f) and g), causing the target sequence to be amplified in situ.

20. The method of claim 19 further comprising detecting the amplified target sequence.

21. The method of claim 20 wherein the sample of cells is selected from the group consisting of cells in suspension and tissue sections.

22. The method of claim 20 wherein the amplified target sequence is detected by in situ hybridization to a detector probe comprising a detectable label.

23. The method of claim 20 wherein the amplified target sequence is detected by hybridizing a primer to the amplified target sequence and extending the primer with a DNA polymerase to synthesize a sequence complementary to the amplified target sequence, wherein the hybridized primer comprises a detectable label, or a detectable label is incorporated into the complementary sequence by incorporating nucleotides comprising a detectable label.

24. The method of claim 23 wherein the primer is 5' end-labeled with $^{32}$P.

25. The method of claim 20 wherein the amplified target sequence is detected by means of exonuclease deficient polymerase incorporation of nucleotides comprising a detectable label into the amplified target sequence.

26. The method of claim 23 or 25 wherein the amplified target sequence is detected by means of a fluorescent label.

27. The method of claim 26 wherein the amplified target sequence is detected by flow cytometry.

28. The method of claim 23 or 25 wherein the amplified target sequence is detected by automated image cytometry.

29. The method of claim 28 wherein the amplified target sequence is detected by means of a detectable label comprising alkaline phosphatase.

30. The method of claim 29 wherein the detectable label is selected from the group consisting of fluorescent labels, digoxigenin and biotin.

31. The method of claim 30 wherein the amplified target sequence is detected by flow cytometry.

32. The method of claim 20 wherein amplification of a DNA target sequence is detected.

33. The method of claim 20 wherein amplification of an RNA target sequence is detected.

34. The method of claim 32 wherein an HIV target sequence is detected.

35. The method of claim 33 wherein an HIV target sequence is detected.

36. A method for in situ detection of an HIV target sequence in a cell comprising the steps of:

a) providing a sample of nonliving cells in which the morphological integrity of the cells is maintained and reagents for use in strand displacement amplification, including primers, deoxynucleoside triphosphates, an exonuclease deficient polymerase, and a restriction endonuclease, can penetrate the cells;

b) within the cells, hybridizing an amplification primer 3' to the HIV target sequence, the amplification primer comprising a restriction enzyme recognition site 5' to a target binding sequence, and hybridizing an external primer 5' to the amplification primer;

c) extending the amplification primer and the external primer in the presence of the exonuclease deficient polymerase and four deoxynucleoside triphosphates, at least one of which is an α-thio deoxynucleoside triphosphate, to produce an amplification primer extension product which is displaced from the target sequence by the extension of the external primer;

d) in the presence of the exonuclease deficient polymerase and deoxynucleoside triphosphates, making the displaced amplification primer extension product double stranded by synthesizing a complementary strand;

e) nicking one strand of the double stranded primer extension product at the restriction enzyme recognition site which recognition site includes the α-thio deoxyribonucleoside triphosphate using the restriction endonuclease;

f) using the strand complementary to the nicked strand as a template, polymerizing a strand from the 3' end produced by the nick with the exonuclease deficient polymerase and the deoxynucleoside triphosphates, whereby the nicked strand is displaced from the template strand;

g) repeating steps e) and f), causing the target sequence to be amplified in situ, and g) detecting the amplified HIV target sequence in situ by flow cytometric analysis of a fluorescent label.

37. The method of claim 36 wherein the fluorescent label is attached to a deoxynucleoside triphosphate and the labeled deoxynucleoside triphosphate is incorporated into the amplified target sequence by the exonuclease deficient polymerase.

38. The method of claim 36 wherein the amplified HIV target sequence is detected by in situ hybridization to a detector probe comprising a detectable label.

39. The method of claim 36 wherein the amplified target sequence is in the HIV gag gene.

40. The method of claim 36 wherein the restriction endonuclease is HincII.

41. The method of claim 1 wherein the sample of cells has been fixed.

42. The method of claim 19 wherein the sample of cells has been fixed.

43. The method of claim 36 wherein the sample of cells has been fixed.

44. The method of claim 19 wherein the restriction endonuclease is HincII.

* * * * *

UNITED STATES PATENT AND TRADEMARK OFFICE
CERTIFICATE OF CORRECTION

PATENT NO. : 5,523,204
DATED : June 4, 1996
INVENTOR(S) : Robert H. Singer, et. al.

It is certified that error appears in the above-indentified patent and that said Letters Patent is hereby corrected as shown below:

Col. 1, line 5, before "FIELD OF THE INVENTION", add the following:
--This work was supported in part by Grant No. HB 67022 from the National Institutes of Health.--;
Col. 3, line 46, replace "971-4975" with 4971-4975--;
Col. 6, line 46, replace "in sire PCR." with --in situ PCR--;
Col. 7, line 27, replace "KNA" with --RNA--;
Col. 11, line 9, replace "in Mtu SDA" with --in situ SDZ--;
Col. 13, line 11, replace "1 gM" with --1 $\mu$M--;
Col. 16, line 45, replace "to the fight" with --to the right--;
Col. 22, claim 36, line 34, replace "endonuclease, can penetrate the cells" with --endonuclease, can penetrate the nonliving cells--.

Signed and Sealed this

Nineteenth Day of November, 1996

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1
        ( B ) STRAIN: HXB-2

( x i ) SEQUENCE DESCRIPTION: SEQ ID NO:1:

```
ATAATCCACC TATCCCAGTA GGAGAAAT                                          28
```

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1
        ( B ) STRAIN: HXB-2

( x i ) SEQUENCE DESCRIPTION: SEQ ID NO:2:

```
TTTGGTCCTT GTCTTATGTC CAGAATGC                                          28
```

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1
        ( B ) STRAIN: HXB-2

( x i ) SEQUENCE DESCRIPTION: SEQ ID NO:3:

```
ATCCTGGGAT TAAATAAAAT AGTAAGAATG TATAGCCCTA C                           41
```

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
AATAGTCGCT TACTTGTTGA CGGATAATCC TGGG                                   34
```

( 2 ) INFORMATION FOR SEQ ID NO:5:

```
    ( i ) SEQUENCE CHARACTERISTICS:
            ( A ) LENGTH: 34 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

AAGTAACCGA CTATTGTTGA CGGCTATACA TTCT                                                        3 4

( 2 ) INFORMATION FOR SEQ ID NO:6:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Human immunodeficiency virus type 1
            ( B ) STRAIN: HXB-2

( x i ) SEQUENCE DESCRIPTION: SEQ ID NO:6:

ACTATTTTAT TTAAACC                                                                            1 7
```